(12) United States Patent
Clemence et al.

(10) Patent No.: US 6,534,515 B2
(45) Date of Patent: *Mar. 18, 2003

(54) 20,21-DINOR-EBURNAMENINES

(75) Inventors: François Clemence, Paris (FR); Jean-Luc Haesslein, Courtry (FR); Claude Oberlander, Paris (FR)

(73) Assignee: Aventis Pharma S.A. (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/228,300

(22) Filed: Apr. 15, 1994

(65) Prior Publication Data

US 2002/0045637 A1 Apr. 18, 2002

Related U.S. Application Data

(63) Continuation of application No. 07/988,212, filed on Dec. 9, 1992, now abandoned, which is a continuation of application No. 07/597,897, filed on Oct. 15, 1990, now abandoned.

(30) Foreign Application Priority Data

Oct. 17, 1989 (FR) .................................... 89 13544

(51) Int. Cl.$^7$ .................. C07D 461/00; A61K 31/475

(52) U.S. Cl. .................................. 514/283; 546/51

(58) Field of Search ........................... 546/51; 514/283

(56) References Cited

U.S. PATENT DOCUMENTS

| | | | | |
|---|---|---|---|---|
| 4,382,936 A | * | 5/1983 | Katsube et al. | 424/256 |
| 4,501,740 A | * | 2/1985 | Clemence et al. | 514/283 |
| 5,034,396 A | * | 7/1991 | Aktogu et al. | 514/283 |
| 5,093,337 A | * | 3/1992 | Aktogu et al. | 514/283 |

* cited by examiner

*Primary Examiner*—John M. Ford
(74) *Attorney, Agent, or Firm*—Bierman, Muserlian and Lucas

(57) ABSTRACT

A compound selected from the group consisting of all possible isomers or racemates of a compound of the formula

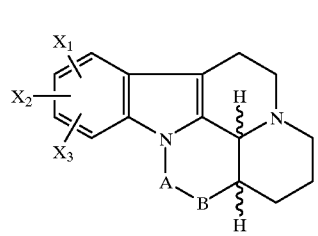

(I)

wherein the various substituents are as defined in the specification and its non-toxic, pharmaceutically acceptable salts with acids or bases having anti-anoxic, anti-ischemic and neuronal protective anti-depressant activities.

10 Claims, No Drawings

20,21-DINOR-EBURNAMENINES

PRIOR APPLICATIONS

This application is a continuation of U.S. patent application Ser. No. 07/988,212 filed Dec. 9, 1992 which is a continuation of U.S. patent application Ser. No. 07/597,897 filed Oct. 15, 1990, both now abandoned.

It is an object of the invention to provide the novel 20,21-dinor-eburnamenines of formula I and their non-toxic, pharmaceutically acceptable salts and a novel process and novel intermediates for their preparation.

It is another object of the invention to provide novel pharmaceutical compositions and methods.

These and other objects and advantages of the invention will become obvious from the following detailed description.

THE INVENTION

The novel compounds of the invention are a compound selected from the group consistiny of all possible isomers or racemates of a compound of the formula

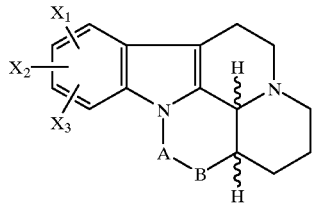

(I)

wherein $X_1$, $X_2$ and $X_3$ are individually selected from the group consisting of hydrogen, halogen, unsubstituted or substituted alkyl of 1 to 18 carbon atoms, unsubstituted or substituted alkenyl and alkynyl of 2 to 18 carton atoms, unsubstituted or substituted alkoxy of 1 to 7 carbon atoms, —OH, —$CF_3$, —$NO_2$, —$NH_2$, mono and dialkylamino of 1 to 5 alkyl carbon atoms and unsubstituted or substituted phenyl,

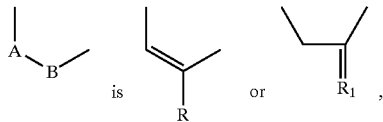

R is selected from the group consisting of unsubstituted or substituted alkyl of 1 to 7 carbon atoms, unsubstituted or substituted alkenyl and alkynyl of 2 to 7 carbon atoms, unsubstituted or substituted phenyl and carboxy optionally salified or esterified, $R_1$ is

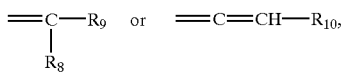

one of $R_8$ and $R_9$ is selected from the group consisting of hydrogen, unsubstituted or substituted alkyl of 1 to 6 carbon atoms, unsubstituted or substituted alkenyl and alkynyl of 2 to 6 carbon atoms, unsubstituted or substituted phenyl, esterified carboxy, —CN, and acyl of 2 to 6 carbon atoms and the other and $R_{10}$ are selected from the group consisting of hydrogen, unsubstituted or substituted alkyl of 1 to 6 carbon atoms, unsubstituted or substituted alkenyl and alky- nyl of 2 to 6 carbon atoms and unsubstituted or substituted phenyl and its non-toxic, pharmaceutically acceptable salts with acids or bases.

In the compounds of formula I, the 3-hydrogen and the 16-hydrogen can each leave the alpha or beta configuration which determines if the compounds will be the cis or trans diastereoisomeric form.

In the compounds of formula I, halogen may be bromine or iodine but is preferably chlorine or fluorine. Examples of alkyl are methyl, ethyl, n-propyl, isopropyl, n-butyl, isobutyl, sec-butyl, tert.-butyl and n-penityl and examples of alkoxy are methoxy, ethoxy, n-propoxy, isopropoxy and n-butoxy, tert.-butoxy. Examples of monoalkyl and dialkylaminio of 1 to 5 alkyl carbon atoms include methylamino, dimethylamino, ethylamino, diethylamino and isopropyl amino.

Examples of alkenyl and alkynyl include vinyl, allyl, 1-propenyl butenyl, pentenyl, ethynyl, propargyl, butynyl and pentynyl. Examples of acyl of 1 to 6 carbon atoms include formyl, acetyl, propionyl, butytyl, benzoyl, valeryl, hexanoyl, acryloyl, crotonoyl and carbamoyl. Examples of esterified carboxy are lower alkoxycarbonyls such as methoxycarbonyl, ethoxycarbonyl or benzyloxycarbonyl.

Examples of suitable acids to form the non-toxic, pharmaceutically acceptable acid addition salts are inorganic acids such as hydrochloric acid, hydrobromic acid, hydroiodic acid, nitric acid, sulfuric acid, phosphoric acid, and organic acids such as propioniic acid, acetic acid, formic acid, bezizoic acid, maleic acid, fumaric acid, succinic acid, tartaric acid, citric acid, oxalic, acid, glyoxylic acid, aspartic acid, ascorbic acid, alkylmonosulfonic acids such as metlanesulfonic acid, ethanesulfonic acid and propanesulfoniic acid alkyldisulfonic acids such as methanedisulfonic acid, α,β-ethane-disulfonic acid, arylmonosulfonic acids such as benzenesulfonic acid and aryldisulfonic acids.

When R is carboxy, it can be salified by a base to form a salt of sodium, potassium, lithium, calcium, magnesium or ammonium or salts with organic bases such as methylamine, propylamine, trimethylamine, diethliylamine, triethylamine, N,N-dimethylethanolamine, tris (hydroxy-methyl) aminomethane, ethanolamine, pyridine, picoline, dicyclohexylamine, morpholine, benzylamine, procaine, lysine, arginine, histidine and N-methylglucamine.

The alkyl, alkenyl or alkynyl can be substituted with at least one member of the group consisting of hydroxy, aryl such as phenyl or naphthyl; arylalkyl such as benzyl or phenethyl; cycloalkyl, cyclo-pentyl or cyclohexyl; alkoxy such as methoxy, ethoxy, propoxy or isopropoxy, methoxymethyl or 1-ethoxyethyl; aryloxy such as phenoxy; (aralkoxy such as benzyloxy; mercapto; alkylthio such as methylthio or ethylthio; anylthio; aralkylthio; amino such as 2-amineoethyl; substituted amino such as methylamino, ethylamino or dimethylamino; halogen i.e., chloro or bromo, such as 2-bromoethyl; nitro; azido; carbamoyl; substituted carbamoyl such as a lower N-monoalkyl carbamoyl group like N-methylcarbamoyl, N-ethylcarbamoyl, a lower N,N-dialkyl carbamoyl such as N,N-dimethylcarbamoyl, N,N-diethylcarbamoyl; an N-(lower hydroxyalkyl) carbamoyl such as N-(hydroxymethyl) carbamoyl, N-(hydroxyethyl) carbamoyl, a lower carbamoylalkyl such as carbamoylmethyl, carbamoylethyl; carboxy; esterified carboxy such as methoxycarbonyl or ethoxycarbonyl; formyl; acyl such as acetyl, propionyl or benzoyl; acyloxy such as acetoxy or propionyloxy; cyano; phthlalimido; acylamido such as acetamido or benzamido; alkoxycarbonylamino such as methoxycarbonylamino or ethoxycarbonylamino; or (arylalkyl)-oxycarbonylamino such as benzyloxycarbonylamino.

A The aryl and aralkyl can be unsubstituted or substituted with at least one member of the group consisting of hydroxy; halogen; alkyl such as methyl, ethyl, isopropyl or tert-butyl; alkoxy such as methoxy, ethoxy or isopropoxy; alkylthio such as methylthio or ethylthio; nitro; amino; substituted amino such as monoalkylamino and dialkylamino such as methylamino, ethylamino or dimethylamino.

When $X_1$, $X_2$ or $X_3$ are substituted alkyl or alkoxy, this is preferably substituted by at least one hydroxy, free or esterified carboxy such as methoxycarbonyl or ethoxycarbonyl, and the alkyl may be substituted by a liner or branched alkoxy of 1 to 5 carbon atoms like methoxy, ethoxy or isopropoxy.

Among the preferred compounds of formula I are those wherein $X_1$, $X_2$ and $X_3$ are hydrogen, those wherein the alkyl, alkoxy, alkenyl and alkynyl are substituted with at least one member of the group consisting of —OH, halogen, alkoxy of 1 to 6 carbon atoms, acyl of an organic carboxylic acid of 1 to 6 carbon atoms, benzoyl, —CN, carboxy, carboxy esterified with an alkanol of 1 to 5 carbon atoms, unsubstituted or substituted phenyl, unsubstituted or substituted carbamoyl and

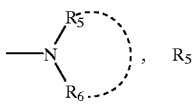, $R_5$ and $R_6$ are individually selected from the group consisting of hydrogen, alkyl of 1 to 7 carbon atoms unsubstituted or substituted by at least one member of the group consisting of —OH, alkoxy of 1 to 5 carbon atoms and free carboxy or esterified with alkyl of 1 to 5 carbon atoms and unsubstituted or substituted aryl of 6 to 12 carbon atoms and aralkyl of 7 to 12 carbon atoms or taken together with the nitrogen to which they are attached form a 5 to 6 member heterocycle containing or not a second heteroatom selected from the group consisting of —O—, —S— and —$NR_A$ and —$R_A$ is selected from the group consisting of hydrogen, alkyl and hydroxy-alkyl of 1 to 5 carbon atoms, halogen, alkoxy of 1 to 4 carbon atoms, unsubstituted or substituted aryl of 6 to 12 carbon atoms and unsubstituted or substituted aralkyl of 7 to 12 carbon atoms and their non-toxic, a pharmaceutically acceptable acid addition salts.

Other preferred compounds of formula I are those wherein the phenyl, aryl and aralkyl are substituted with at least one member of the group consisting of halogen, —OH, alkyl and alkoxy of 1 to 5 carbon atoms, $CH_3S$—, —$NO_2$, —$NH_2$ and monoalkyl and dialkylamino. Aralkyl of 7 to 12 carbon atoms is preferably benzyl or phenethyl unsubstituted or substituted with at least one member of the group consisting of methyl, ethyl, isopropyl, tert.-butyl, methoxy, ethoxy or propoxy.

Examples of

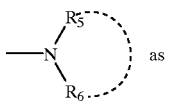 as as a heterocyclic are pyyrolidino, piperidino, morpholino, piperazinyl, methylpiperazinyl, ethylpiperazinyl, propylpiperazinyl, phenylpiperazinyl or benzylpiperazinyl. When $R_5$ and $R_6$ represent the latter two, the phenyl and benzyl can be optionally substituted by the substituents already mentioned for aryl and aralkyl.

Examples of specific preferred compounds of formula I are

[$16_\alpha$, (±)]-15-(1-propynyl)-20,21-dinoreburnamenine oxalate,

[$16_\alpha$, (±)]-15-methyl-20, 21-dinoreburnamenine,

[$16_\alpha$, (±)]-14,15-dihydro-15-methylene-20, 21-dinoreburnamenine acid maleate, ethyl [$16_\alpha$, (±)-20,21-dinoreburnamenine-15-acetate maleate,

[$16_\alpha$, (±)-20,21-dinoreburnamenine-15-methanol acid maleate and

[$16_\alpha$, (±)]-N,N-dimethyl-20,21-dinoreburnamenine-15-methanamine acid maleate.

The novel process of the invention for the preparation of the compounds of formula I comprises reacting a compound of the formula

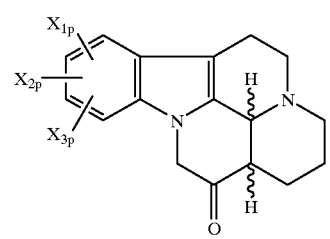

(II)

in which $X_{1p}$, $X_{2p}$ and $X_{3p}$ are $X_1$, $X_2$ and $X_3$ as defined above in which the reactive functions are optionally protected with A) either a halide of the formula

R'—V-Hal   III wherein V is magnesium or zinc and Hal is halogen or an organometallic compound of the formula

R'—W   IV wherein W is lithium, sodium or potassium and R' is R either except for the free, salified or esterified carboxy or R in which the reactive functions are protected to obtain a compound of the formula

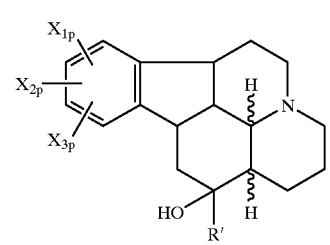

(V)

wherein R' has the above meaning and subjecting the latter to a dehydration reaction and, if necessary, to an elimination reaction of the protector groups of the reactive functions which can be carried by $X_{1p}$, $X_{2p}$, $X_{3p}$ and R' to obtain a compound of the formula

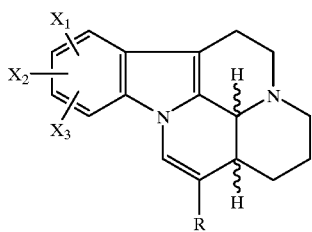

(Ia₁)

wherein $X_1$, $X_2$, $X_3$ and R have the above meanings, optionally subjecting the latter when R is —CH$_2$OH to the action of an oxidizing agent to obtain a product of the formula

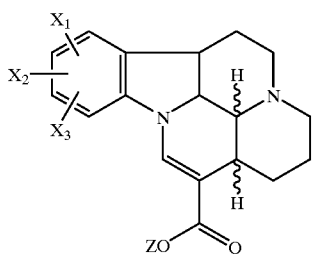

(Ia₂)

wherein $X_1$, $X_2$, $X_3$ have the above meanings and Z is hydrogen or the remainder of an ester group, which is optionally subjected to one or both of the following reactions: hydrolysis of the ester group and esterification or salification by a base of the carboxylic function.

B) or a derivative of triphenylphosphoranle of the formula

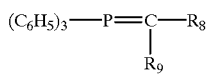

VI or a phosphonate of the formula

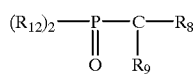

VI' wherein $R_{12}$ is alyoxy and $R_8$ $_{and\ R9}$ have the meanings indicated above to obtain according to the operating conditions used and optionally after elimination of the protector groups of the reactive functions which can be carried by $X_{1p}$, $X_{2p}$ and $X_{3p}$ a compound of the formula

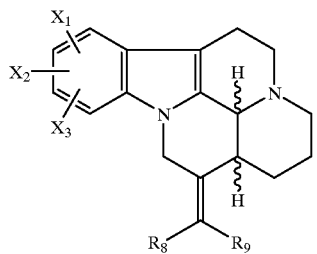

(Ib₁)

or a compound of the formula

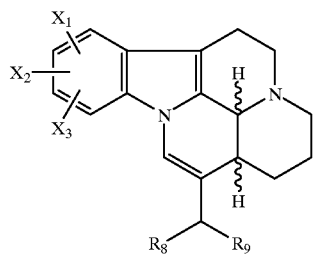

(Ia₃)

wherein $X_1$, $X_2$, $X_3$, $R_8$ and $R_9$ have the above meanings.

C) or an activated derivative of the product of the formula $$R_{10}\text{—C}\equiv\text{CH} \qquad \text{VII}$$

in which $R_{10}$ as the above meaning to obtain a compound of the formula

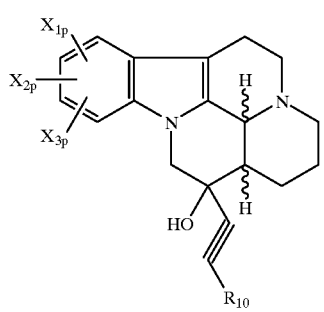

(VIII)

in which $X_{1p}$, $X_{2p}$, $X_{3p}$ and $R_{10}$ have the above meanings which is subjected, after activation of the hydroxyl and optional protection of the reactive functions which $R_{10}$ can contain, to a reduction reaction, and optionally to an elimination reaction of the protector groups of the protected reactive functions to obtain a compound of the formula

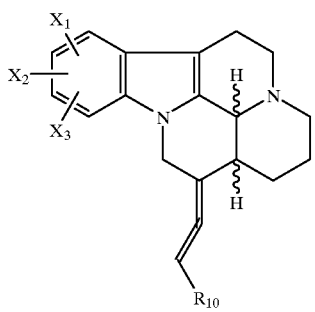

(Ib2)

in which $X_1$, $X_2$, $X_3$ and $R_{10}$ have the above menaings and optionally the products of formulae $I_{a1}$, $I_{a3}$, $I_{b1}$ and $I_{b2}$ are treated with a mineral or organic acid to obtain the corresponding salt, the said products of formula I being in all the possible racemic or enantiomeric isomer forms.

In the preferred conditions for the process of the invention, in the reaction as defined above in A), the preparation of the organomagnesium or zinc compounds of formula III and their reaction with a product of formula II can be carried out in the usual conditions known. The halogen of the magnesium or zinc halide of formula III can be bromine such as in phenylmagnesium bromide but it can also be an iodine or chlorine atom.

The preparation of the magnesium halide can be carried out, for example, by the reaction of magnesium with an organic halide in a slightly polar inert medium such as ether by the preparation process for organomagnesilm halides or Grignard reagents. The reaction of the product of formula II with the magnesium halide of formula III to obtain the products of formula V takes place preferably in an organic solvant such as ether or tetrahydrofuran at ambient temperature or under reflux.

The preparation of organometallic compounds of formula IV in which W is lithium, sodium or potassium, and their reaction with a product of formula II can be carried out in the usual conditions known. The preparation of the organolithium compound of formula IV can be effected by the reaction of an organic halide with a base such as, preferably, diisopropyllithium amide or butyllithium, for example in ether or tetrahydrofuran at a low temperature. The reaction of the product of formula II with the organolithium compound of formula IV can be effected in tetrahydrofuran or ether at a low temperature of $-70°$ C. to $-10°$ C. or also in dimethoxymethane.

The dehydration of the product of formula V to obtain a product of formula $I_{a1}$ takes place in an organic solvent which is preferably toluene or xylene, but may also be tetrahydrofuran in the presence of, for example, $P_2O_5$ or also Burgess salts. This dehydration reaction can also be effected by the activation of alcohol preferably into mesylate by methanesulfonyl chloride followed by a treatment with a strong base such as, preferably diazabicycloundecene or diazabicyclononene.

The oxidation of the product of formula $I_{a1}$ leading to the product of formula $I_{a2}$ is effected by the usual methods using for example chromium salts, selenium oxide or by operating according to Swern's reaction. The hydrolysis of the ester group, the optional esterification or salification of the product of formula $I_{a2}$ is effected according to the usual methods.

In the reaction of B) 1), the tripheniylpliosphorane of formula VI is formed by the reaction of triphenylphosphine with the corresponding halide in which the halogen atom is preferably bromine and leading to a phosphonium salt on which a base such as potassium tert-butylate or butyllithium is reacted to obtain the expected product of formula VI. The reaction is carried out in an organic solvent such as tetrahydrofuran or ether at a temperature of between $0°$ C. and reflux.

The reaction of the product of formula II with the triplienylphosphorane of formula VI to obtain a product of formula $I_{b1}$ is carried out at a temperature of between $-70°$ C. and $0°$ C. The preparation of the reagent of formula VI and its reaction with the product of formula II are carried out by standard methods.

The reaction of the product of formula II and the phosphonate of formula VI' to obtain the product of formula $I_{b1}$ is carried out in the presence of sodium hydride or a weak base such as sodium or potassium carbonate in a solvent such as tetrahydrofuran. When a mole to mole mixture of the product of formula II and the phosphonate of formula VI' is used, the desired compounds of formula $I_{b1}$ will for the most part be obtained, while an excess of ylide and a basic medium lead for the most part to compounds of formula $I_{b3}$.

In the preferred conditions for implementing the reaction, the phosphorated derivative used to obtain compounds of formula $I_{b1}$ in which $R_8$ and $R_9$ are an optionally substituted alkyl or phenyl is a phosphorane. In the cases where $R_8$ and $R_9$ contain one or more ester, cyano or acyl, the phosphorus-containing derivative used is preferably a phosphonate.

In the reaction as in C) of the product of formula II with an acetylene derivative of formula VII to obtain a compound of formula VIII, the acetylene derivative such as acetylene or propyne is activated in anion form in a basic medium, for example of sodium or potassium alkanoate such as potassium tert-butanoate or of a lithium-containing base such as butyllithium. The reaction takes place in an organic solvent such as tetrahydrofuran or ether. In the reaction as in C), the reduction of the product of formula VIII is carried out with a hydride, notably a mixed hydride, such as lithium and aluminum mixed hydride or sodium and aluminum diethylhydride. Sodium or potassium borohydride can also be used as the reagent as well as sodium cyanoborohydride in the presence of an alcohol such as for example methanol or ethanol.

The activation of the hydroxyl function of the compound of formula VIII can be effected for example by a halide such as, preferably, methanesulfonyl chloride in a basic medium, for example triethylamine or pyridine in an organic solvent such as tetrahydrofuran or dichloromethane. The reduction reaction of the activated compound of formula VIII to obtain tht compounds of formula $I_{b2}$ is preferably effected in anhydrous conditions, for example with a lithium and aluminum hydride in tetrahydrofuran or ether.

In the case where $R_{10}$ contains one or more esterified carboxy functions, these can, by reduction of the compound of formula VIII, be converted into alcohol functions, and in this case these alcohol functions can be optionally re-oxidized to produce the initial esterified carboxy functions. This re-oxidization can be effected by chromium oxide or chromium salts such as pyridinium dichromate or pyridinium chlorochromate in a solvent such as dichloromethane or dimethylformamide.

The process for the preparation of the compounds of formula I wherein

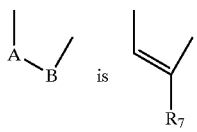 is 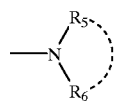

wherein $R_7$ is methyl unsubstituted or substituted with —OH or halogen or free, esterified or salified carboxy or

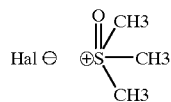

and $R_5$ and $R_6$ are defined as above comprises reacting a compound of the formula (II)

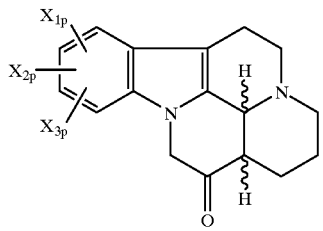

wherein $X_{1p}$, $X_{2p}$, and $X_{3p}$ have the above definitions with a halogenated derivative of methyloxosulfonium of the formula (IX)

$$\text{Hal}^{\ominus} \quad \overset{O}{\underset{CH_3}{\overset{\|}{\oplus S}}}{-}CH_3$$

in a basic medium to obtain the corresponding epoxide of the formula (X)

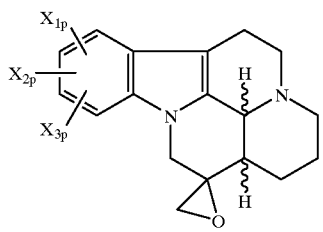

wherein $X_{1p}$, $X_2$ and $X_3$ have the above meanings and reacting the latter either with a base to obtain the corresponding alcohol of the formula (X')

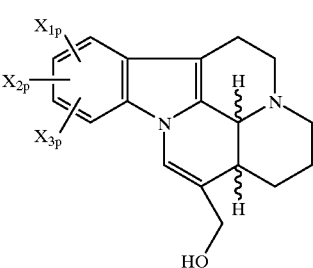

in which $X_{1p}$, $X_{2p}$ and $X_{3p}$ have the above meanings and optionally subjecting the latter to an elimination reaction of the protector groups of the reactive functions that can be carried by $X_{1p}$, $X_{2p}$ and $X_{3p}$ to produce a product of the formula (Ia$_4$)

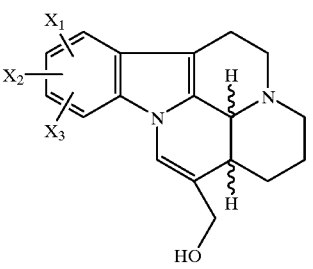

in which $X_1$, $X_2$ and $X_3$ have the above meanings and optionally treating the latter with an oxidizing agent to obtain a product of the formula (Ia$_2$)

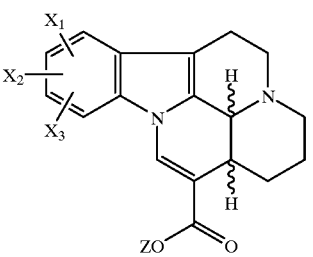

in which $X_1$, $X_2$, $X_3$ and Z have the above meanings which is optionally subjected to one or both of the following reactions: hydrolysis of the ester group and esterification or salification by a base of the carboxy function, or with an amine of the formula

XI

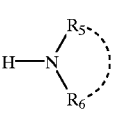

in which $R_5$ and $R_6$ have the above meanings to obtain a compound of the formula

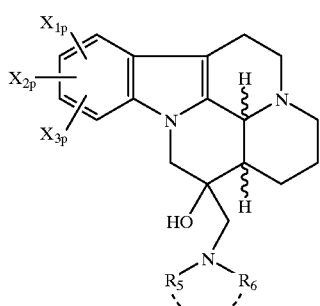

(XII)

in which $X_{1p}$, $X_{2p}$ and $X_{3p}$ have the above meanings, the said compounds of formula X' and XII being subjected, after activation of the hydroxyl either, if desired in the case of compound X', to a reaction with the amine of formula XI as defined above, or, in the case of compound XII to a dehydration reaction to obtain in these two cases and after elimination, if necessary, of the protector groups of the reactive functions which can be carried by $X_{1p}$, $X_{2p}$ and $X_{3p}$ a compound of the formula

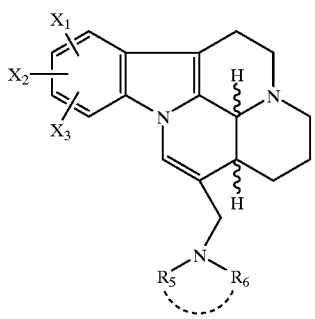

(Ia5)

in which $X_1$, $X_2$, $X_3$, $R_5$ and $R_6$ have the above meanings or with a tetrabutylammonium halide to obtain a product of the formula

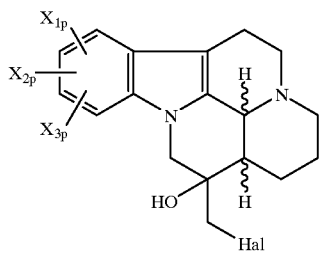

(XIII)

in which Hal is halogen, then subjecting the latter to a dehydration reaction to obtain, after elimination if necessary of the protector groups or the reactive functions which can be carried by $X_{1p}$, $X_{2p}$ and $X_{3p}$ a compound of the formula

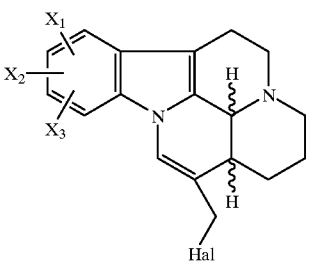

(Ia6)

in which $X_1$, $X_2$, $X_3$ and Hal have the above meaning, and if desired the products of formulae $I_{a3}$, $I_{a5}$ and $I_{a6}$ are treated with a mineral or organic acid to obtain the corresponding acid addition salt, the said products of formula I being in all the possible racemic and enantiomeric isomer forms.

In the preferred mode of the process of the invention, the reaction of the product of formula II with the halogenated derivative of methyloxosulfonium of formula IX, such as for example trimethyloxosulfonium iodide to obtain the compounds of formula X is carried out in a basic medium, for example potassium tert-butylate or butyllithium in the presence of an organic solvent such as tetrahydrofuran or ether.

The start of the reaction of epoxide of formula X leading to the product of formula X' is carried out for example in a solution of lithium diisopropylamide in tetrahydrofuran at a temperature of about −70° C., which is then allowed to return to ambient temperature.

The oxidation of the product of formula $I_{a4}$ leading to the product of formula $I_{a2}$ is carried out as indicated above for the oxidation of the products $I^{a1}$. The hyrolysis of the ester group, the optional esterification or salification are carried out according to known methods.

The starting reaction of the epoxide of formula X with the addition of the amnine of formula XI leading to the compound of formula XII is carried out in an alcohol solvent such as methanol or ethanol at reflux of the alcohol used.

The hydroxyl of the compounds of formula X' and XII can be activated using for example mesyl chloride or trifluoroacetyl chloride in a solution of tetrahydrofuran in the presence of a base such as pyridine or triethylamine. The dehydration of the activated compound of formula XII leading to the product of formula $I_{a5}$ is carried out in an organic solvent such as toluene in the presence of a strong base such as diazabicycloundecene or diazabicyclononene at reflux. The product of formula $I_{a5}$ can also be obtained by the addition of the amine of formula XI on the activated compound of formula X'. The reaction takes place in a solvent such as toluene or xylene or an alcohol such as methanol or ethanol, the mixture being taken to reflux.

The halide which is used to obtain a product of formula XIII is for example tetrabutylammonium fluoride in an organic solvent.

The process of the invention for the preparation of a compound of formula I wherein

is 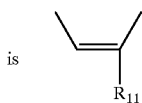

wherein $R_{11}$ is —C≡C—$R_{10}$ and $R_{10}$ is defined as above comprises reacting a compound of the formula

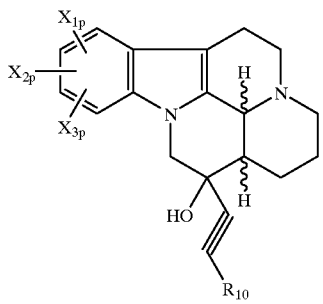

(VIII)

wherein $X_{1p}$, $X_{2p}$, $X_{3p}$ and $R_{10}$ have the above meaning after activation of the hydroxyl with a dehydration agent to obtain, after elimination, if necessary and if desired, of the protector groups of the reactive functions which can be carried by $X_{1p}$, $X_{2p}$ and $X_{3p}$ a compound of the enyne type of the formula

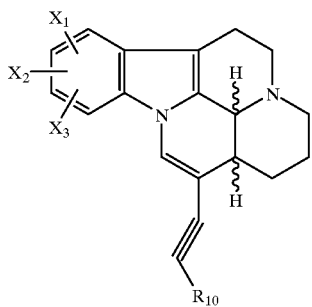

(Ia$_7$)

wherein $X_1$, $X_2$, $X_3$ and $R_{10}$ have the above meanings and if desired the latter product is treated with a mineral or organic acid, the said products of formula I being in all the possible racemic or enantiomeric isomer forms.

The dehydration reaction of the compound of formula VIII activated on the hydroxyl, for example, into the mesylate or acetate, is carried out preferably in an organic solvent such as toluene in the presence of a base such as diazabicyclo-undecene or diazabicyclononene. The various reactive functions which can be carried by certain compounds above can, if necessary, be protected: for example free hydroxyl, acyl, or carboxy or amino and monoalkylamino which can be protected by the appropriate protectors.

The following non-exhaustive list of examples of protection of reactive functions can be cited: the hydroxy groups can be protected for example by trimethylsilyl, tert-butyldimethylsilyl, dihydropyran or metlhoxymethyl; the amino groups can be protected for example by trityl, benzyl, tert-butoxycarbonyl, or phthalimido or by other groups known in the chemistry of peptides; the acyl groups such as formyl can be protected for example in the form of cyclic or non-cyclic ketals such as dimethyl- or diethyl ketal or ethylene dioxyketal; and the carboxys can be protected for example in the form of esters formed with easily cleavable esters such as benzyl or tert-butyl esters.

The elimination of these protectors groups is carried out under the usual conditions known to a man of the art, notably acid hydrolysis carried out with an acid such as one of the following acids: hydrochloric acid, benzene sulfonic acid, or para-toluene sulfonic acid, formic acid or trifluoroacetic acid. The phthalimido group is eliminated by hydrazine. A list of the various usable protector groups will be found for example in Pat. No. 2,499,995.

The optically active forms of the products of formula I can be recovered by resolution of the racemates by the usual methods or using as starting products, products of formula II in optically active forms.

The novel pharmaceutical compositions of the invention are comprised of a pharmaceutically effective amount of at least one compound of formula I or its salts and an inert carrier. The compositions may be in the form of tablets, dragees, capsules, granules, suppositories, ointments, creams, gels, aerosols and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

The compositions have an affinity for the adrenergic alpha2 receptors and also have useful anti-amnesic, neuronal protective anti-depressant, anti-anoxic or anti-ischemic properties. They can be used in the treatment of cerebral insufficiencies of anoxic or ischemic origin, of menory and attention disorders as well as can be used as anti-depressants.

The novel method of the invention comprises administering to warm-blooded animals, including humans, an effective amount of at least one compound of formula I and its salts. The compounds may be administered orally, rectally, buccally, parenterally or topically to the skin and mucous membrane. The usual daily dose is 0.1333 to 2.666 mg/kg depending on the condition treated, the method of administration and the specific compound.

The starting compound of formula II$_a$ in which $X_1$, $X_2$ and $X_3$ are hydrogen is described in U.S. Patent No. 4,382,936. The starting compounds of the formula

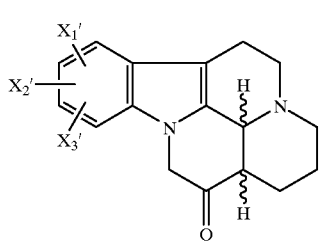

II' in which $X_{1'}$, $X_{2'}$ and $X_{3'}$ are individually $X_1$, $X_2$ and $X_3$ and at least one of $X_{1'}$, $X_{2'}$, and $X_{3'}$ is not hydrogen can be prepared by the process described in the said patent starting from corresponding substituted tryptamines.

Another process for the products of formula II' as defined above consists of subjecting the product of the formula

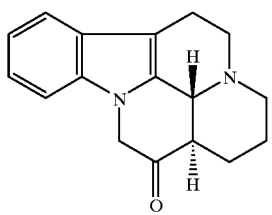

IIa to a nitration reaction to obtain a product of formula

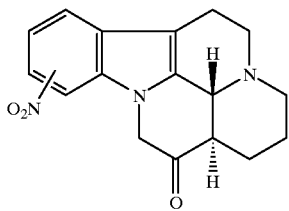

IIb which is reduced, if appropriate, to obtain a product of the formula

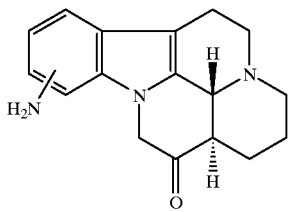

IIc which, if appropriate either is subjected to an alkylation or acylation reaction, or is converted to a diazonium salt from which there is prepared by known processes, the derivatives of the formula

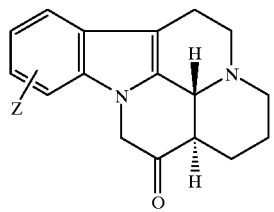

IId wherein Z is halogen or an optionally substituted hydroxy or phenyl, which are converted, if appropriate, into corresponding derivatives in which Z is alkyloxy or alkyl.

Finally as new industrial products as intermediates necessary for the preparation of products of formula I are the compounds of the formula

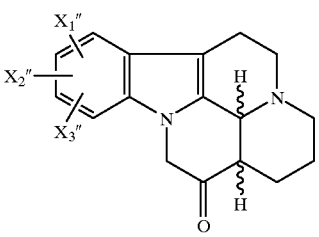

(II'')

in which $X_1''$, $X_2''$ and $X_3''$ are individually $X_1$, $X_2$ and $X_3$, except for the products in which one of the substituents $X_1''$, $X_2''$ and $X_3''$ is hydrogen and the other two are individually chosen from hydrogen or halogen, alkyl or alkoxy of 1 to 5 carbon atoms, hydroxy, trifluoromethyl or nitro and the compounds of formulae V, VIII, X, X', XII and XIII.

In the following examples, there are described several preferred embodiments to illustrate the invention. However, it should be understood that the invention is not intended to be limited to the specific embodiments.

EXAMPLE 1

[16α, (+)]-15-ethynyl-20,21-dinoreburniamenine

STEP A: [16α, (±)]-14,15-dihydro-15-ethynyl-20,21-dinoreburnamenin-15-ol

Acetylene was bubbled through 600 ml of a molar solution of potassium tertbutylate in tetrahydrofuran for 30 minutes at 0° C. and then a solution of 6 g of [16α(±)]-20,21-dinoreburnamenin-15(14H)-one in 140 ml of tetrahydrofuran was added at 0° C. The mixture was stirred for 3 hours at ambient temperature, then poured into water and extracted with methylene chloride. The extracts were dried and evaporated to dryness under reduced pressure to obtain 5.4 g of expected product which was used as is for the following step.

STEP B: [16α, (±)]-14,15-dihydro-15-ethynyl-20,21-dinoreburnamin-15-methanesulfonate 3.7 ml of triethylamine were added to a solution of 3.1 g of the product of Step A in 125 ml of tetrahydrofuran and the mixture was stirred for 20 minutes and 0.8 ml of methane sulfonyl chloride was added slowly. The mixture was stirred for 90 minutes at ambient temperature, followed by filtering and concentrating the filtrate to dryness to obtain 3.8 g of the expected product which was used as is for the following step.

NMR: (CDCl$_3$) 250 MHz

| | |
|---|---|
| N—CH$_2$—C | 5.18 ppm (d, j = 11 Hz) |
| —O-Mes | 3.28 (s) |
| acetylene | 3.06 (s) |
| aromatics | 7.1 to 7.5 (m) |

STEP C: [16α, (±)]-15-ethynyl-20,21-dinoreburnamenine 3.2 ml of diazabicyclo-(5,4,0]-undec-7-ene (DBU) were added to a solution of 3.8 g of the product of Step B in 125 ml of toluene and the mixture was stirred for 20 hours at ambient temperature, then for 8 hours at 50° C. The toluene was evaporated off and the residue was taken up in 200 ml of ethyl acetate, washed with water, dried and evaporated to dryness. The 4.2 g of residue were chromatographed on silica, (eluant: methylene chloride - methanol (98-2)) to obtain 2.3 g of the product which was again chromatographed on silica, (eluant: hexane - ethyl acetate (8-2)) to obtain 1.6 g of the desired product melting at 106° C.

| IR Spectrum (CHCl$_3$) | |
|---|---|
| —C≡C—H | 3306 cm$^{-1}$ |
| Bohlmann bands | |
| Conjugated system | 1654 cm$^{-1}$ |
| | 1615 cm$^{-1}$ |
| Aromatics | 1594 cm$^{-1}$ (F) |
| | 1569 cm$^{-1}$ (fine) |

EXAMPLE 2

[16α, (±)]-15-(1-propynyl)-20,21-dinoreburnamenine and its oxalate

STEP A; [16α, (±)]-14,15-dihydro-15-(1-propynyl)-20,21-dinoreburnamenin-15-ol

Using the procedure of Step A of Example 1, 3 g of [16α, (+)]-20,21-dinoreburnamenin-15-(14H)-one and propyne in place of acetylene were reacted to obtain 2.01 g of the desired product melting at>260° C., after making it into a paste in acetone which was used as is for the following step.

STEP B: [16α, (±)]-14,15-dihydro-15-(1-propynyl)-20,21-dinoreburnamenin-15-methane-sulfonate Using the procedure of Step B of Example 1, 0.750 g of the product of Step A were reacted to obtain 0.6 g of the expected product which was used as is for the next step.

STEP C: 16α, (±)]-15-(1-propynyl)-20,21-dinoreburnamenine and its oxalate 0.22 ml of diazabicyclo-[5,4,0]-undec-7-ene (DBU) were added to a solution of 0.6 g of the product of Step 3 in 30 ml of toluene, and the mixture was stirred for 20 hours at 50° C. The toluene was evaporated off and the residue was chromatographed on silica (eluant: ethyl acetate - liexane (8-2)) to obtain 0.270 g of the desired product in the form of a base melting at >260° C.

Salification: 32 mg of oxalic acid in solution in 2 ml of hot ethyl acetate were added to a solution of 0.1 g of the product above in 20 ml of hot ethyl acetate. After stirring for 4 hours at ambient temperature, the mixture was filtered and the filtrate was washed with 10 ml of ethyl acetate to obtain 0.097 g of the desired product melting at 220° C.

| Analysis: | C$_{20}$H$_{20}$N$_2$, C$_2$H$_2$O$_4$ | | |
|---|---|---|---|
| Calculated: | % C 69.82 | % H 5.86 | % N 7.4 |
| Found: | 69.7 | 5.7 | 7.2 |
| IR Spectrum (CHCl$_3$) | | | |
| C═C | 1652 cm$^{-1}$ | | |
| + | 1596 cm$^{-1}$ | | |
| Aromatics | 1563 cm$^{-1}$ | | |
| Bohlmann bands | | | |

EXAMPLE 3

[16α, (±)]-14,15-dihydro-15-ethenylidene-20,21-dinoreburnamenine and its maleate A solution of 0.44 g of the product of Step B of Example 1 in 70 ml of tetrahydrofuran was added slowly, without exceeding 50° C., to a suspension of lithium aluminium hydride in 30 ml of tetrahydrofuran and the mixture was stirred for 20 hours at ambient temperature. The excess hydride was destroyed with 15 ml of a mixture of tetrahydrofuran and water (⅔-⅓) and the tetrahydrofuran was evaporated off. The residue was taken up in 100 ml of ethyl acetate, filtered on charcoal and the filtrate was washed with water, dried and evaporated to dryness. The 0.650 g of residue were chromatographed on silica (eluant: methylene chloride - methanol (98-2) to obtain 0.210 g of the expected product in the form of a base melting at 138° C.

Salification: 88 mg of maleic acid in solution in 5 ml of ethyl acetate were added hot to a solution of 0.210 g of the base above in 100 ml of ethyl acetate. The mixture was stirred for 2 hours at ambient temperature and after filtering, the filtrate was washed with 3 ml of ethyl acetate to obtain 0.240 g of the desired product melting at 196° C.

| Analysis: | C$_{19}$H$_{20}$N$_2$, C$_4$H$_4$O$_4$ | | |
|---|---|---|---|
| Calculated: | % C 70.39 | % H 6.16 | % N 7.13 |
| Found: | 70.2 | 6.1 | 7.0 |
| IR Spectrum (CHCl$_3$) | | | |

1963 cm$^{-1}$  

EXAMPLE 4

[16α, (±)]-15-phenyl-20,21-dinoreburnamenine and its maleate

STEP A: [16α, (±)]-14,15-dihydro-15-phenyl-20,2-dinoreburnamenine-15-ol 21.6 ml of plienyl bromide in solution in 200 ml of ether were added to a suspension of 5.34 g of magnesium in 50 ml of ether and the mixture was stirred at ambient temperature until the magnesium had completely disappeared (about 4 hours). After cooling to 10° C., 10 g of (16α) 20,21-dinoreburamenin-15(14H)-one (EP 0,013,315) in solution in 300 ml of tetraliydrofuran were added over 50 minutes at +10° C. The mixture was stirred for 20 hours at ambient temperature, poured into 400 ml of water containing ammonium chloride and extracted with ethyl acetate. The extracts were dried and evaporated to dryness under reduced pressure. The 13 g of residue were chromatographed on silica (eluant: metliylezie chloride - acetone (8-2)) to obtain 2.05 g of the expected product (isomer A) melting at >260° C.

STEP B: [16α, (±)]-15-phenyl-20,21-dinoreburnameine and its maleate 0.66 g of phosphorus pentoxide were added to a suspension of 0.8 g of the product of Step A in 30 ml of anhydrous toluene and the mixture was refluxed for 7 hours, cooled and poured into 150 ml of water, then alkalized with concentraded ammonium hydroxide and extracted with ethyl acetate. The extracts were washed with water, dried and evaporated to dryness under reduced pressure. The 0.8 g of residue were chromatographed on silica (eluant: methylene chloride - ethyl acetate (9-1)) to obtain 0.350 g of the desired product in the form of a base melting at 148° C.

Salification: 0.6 of the base above were dissolved in 20 ml of hot ethyl acetate and 0.525 g of maleic acid were added. The mixture was stirred for 2 hours at ambient temperature and was separated and washed with 3 ml of ethyl acetate to obtain 0.785 g of the desired product melting at 260° C.

| | | | |
|---|---|---|---|
| Analysis: | $C_{23}H_{22}N_2$, $C_4H_4O_4$ | | |
| Calculated: | % C 73.28 | % H 5.92 | % N 6.33 |
| Found: | 73.6 | 5.9 | 6.1 |
| IR Spectrum (CHCl₃) | | | |
| C=C | | 1650 cm⁻¹ | |

Aromatic
$$\begin{cases} 1650 \text{ cm}^{-1} \\ 1612 \text{ cm}^{-1} \\ 1566 \text{ cm}^{-1} \\ 1492 \text{ cm}^{-1} \end{cases}$$

Bohlmann band

EXAMPLE 5

[16α, (±)]-15-methyl-20,21-dinoreburnamenine

Step A: (16α)-14,15-dihydro-15-methyl-20,21-dinoreburnamenin-15-ol

Using the procedure of Step A of example 4, 5.33 g of (16α) 20,21-dinoreburnamenin15-(14H)-one (EP 0,013,315) and 40 ml of a toluene solution (1.5M) of methyl magnesium bromide were reacted to obtain after chromatography on silica (eluant: methylene chloride - acetone (1-1)), 3.6 g of the desired product.

STEP B: [16α, (±)]-15-methyl-20,21-dinoreburnamenine 4.3 ml of triethylamine, then 1.56 g of mesyl chloride were added to a solution of 3.5 g of the product of Step A in 100 ml of tetrahydrofuran and the mixture was stirred for 3 hours at ambient temperature. The insoluble part was filtered off and the filtrate was concentrated to dryness under reduced pressure. The residue was dissolved in 100 ml of dioxane and 3.7 ml of diazabicycloundecene were added, followed by stirring for 16 hours at reflux. The mixture was cooled and stirred for 48 hours at ambient temperature. After evaporating to dryness under reduced pressure, the residue was chromatographed on silica (eluant: methylene chloride - acetone (1-1)) to obtain 0.6 g of the expected product melting at 110° C.

Using the procedure of Example 5 and using the appropriate isomer of 20,21-dinoreburnamenine-15-(14H)-one, the products of the following Examples were obtained:

EXAMPLE 6

(16α)-15-methyl-20,21-dinoreburnmenine melting at 140° C. and having a specific rotation of $[\alpha]_D=+313\pm5°$ (c=0.5% in CHCl₃).

EXAMPLE 7

(3-α)-15-methyl-20,21-dinoreburnameinine melting at 140° C. and having a specific rotation of $[\alpha]_D=311.5°\pm5°$ (c=0.5% in CHCl₃).

Using the procedure of Example 5 and the appropriate alkyl magnesium bromide, the products of the following Examples were obtained.

EXAMPLE 8

[16α(±)]-15-ethyl-20,21-dinoreburnamenine melting at 112° C.

EXAMPLE 9

[16α(±)]15-(1-methylethyl)-20,21-dinoreburnamenine acid maleate melting at 200° C.

EXAMPLE 10

[16α(±)]-14,15-dihydro-15-ethylidene-20,21-dinoreburnamenine and its oxalate 40 ml of tetrahydrofuran were added to a mixture of 2.51 g of potassium tert-butylate and 8.35 g of ethyl-triphenyl phosphonium bromide, perfectly anhydrous, and the mixture was stirred for 30 minutes. 3 g of (16α) 20,21-dinoreburnamenine-15-(14H)-one (EP 0,013,315) in solution in 80 ml of tetrahydrofuran were added and the mixture was stirred for one hour, then filtered. The filtrate was evaporated to dryness and the residue was taken up in ethyl acetate and filtered. The filtrate was evaporated to dryness and the residue was made into a paste in isopropyl ether, filtered and the filtrate was evaporated to dryness. 100 ml of ethyl acetate and 1.008 g of oxalic acid were added to the residue and the oxalate was filtered off, dissolved in water and alkalized with ammonium hydroxide at 0° C. The mixture was stirred for 15 minutes, followed by separation and making into a paste in 60 ml of pentane to obtain 1.8 g of the desired product in the form of a base melting at 138° C.

Salification: 10 ml of ethanol were added at 45° C. to a solution of 1.8 g of the base in 120 ml of ethyl acetate, and the resultant mixture was refluxed. 0.581 g of oxalic acid in solution in 15 ml of hot ethyl acetate and 5 ml of ethanol were added and after stirring for 90 minutes at ambient temperature, the mixture was filtered, and the filtrate was washed with 20 ml of ethyl acetate, then with 3 ml of ethanol to obtain 1.87 g of the desired product melting at 225° C.

| | | | |
|---|---|---|---|
| Analysis: | $C_{19}H_{22}N_2$, $C_2H_2O_4$ | | |
| Calculated: | % C 68.46 | % H 6.56 | % N 7.6 |
| Found: | 68.8 | 6.7 | 7.6 |
| NMR CDCl₃ | 300 MHz | | |
| Δ E/ Δ Z mixture | 35/65 | | |

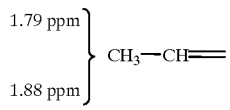 CH₃—CH=

1.79 ppm
1.88 ppm

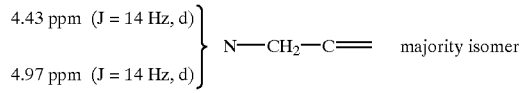

4.43 ppm (J = 14 Hz, d)
4.97 ppm (J = 14 Hz, d)
N—CH₂—C=   majority isomer

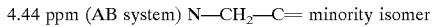

4.44 ppm (AB system) N—CH₂—C= minority isomer

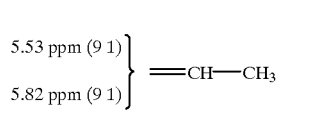 =CH—CH₃

5.53 ppm (9 1)
5.82 ppm (9 1)

from 7.06 to 7.5 ppm (m) 4H: aromatics.

EXAMPLE 11

[16α, (±)]-14,15-dihydro-15-methylene-20,21-dinorburnamenine and its acid maleate Using the procedure of Example 10, 2 g of (16α) 20,21-dinoreburnamenin-15-(14H)-one (EP 0,013,315) and 5.36 g of bromoethyl triphenyl phosphonium were reacted to obtain 2 g of the desired productin the form of a base.

Salification: The 2 g of product obtained above were dissolved in 100 ml of ethyl acetate and 872 mg of maleic acid in solution in 50 ml of refluxing ethyl acetate were added. The mixture was stirred for 2 hours at ambient temperature, separated, and washed with ethyl acetate to obtain 2.32 g of the desired product melting at 208° C.

Analysis:  $C_{22}H_{24}N_2O_4$
Calculated:     % C 69.46    % H 6.36    % N 7.36
Found:               69.4           6.2            7.3
IR Spectrum (CHCl₃)

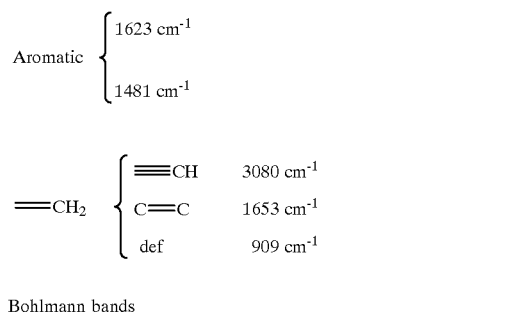

Bohlmann bands

EXAMPLE 12

Ethyl [16α, (±)]-20,21-dinoreburnamenine-15-acetate and its maleate

Using the procedure of Example 10, 2.5 g of (16α)-20,21-dinoreburnamenin-15(14H)-one (EP 0,013,315) and 0.9 g of 50% sodium hydride in oil and 3.72 ml of diethyl phosphonate of ethyl acetate were reacted to obtain 1.1 g of the desired product in the form of a base.

Salification: 0.379 g of maleic acid in solution in 10 ml of hot ethyl acetate were added to a solution of 1.1 g of the base in 60 ml of hot ethyl acetate. After stirring for 2 hours and filtering, the filtrate was washed with ethyl acetate to obtain 1 g of the desired product melting at 180° C.

Analysis: $C_{21}H_{24}N_2O_2 \cdot C_4H_4O_4$
Calculated:     % C 66.36    % H 6.24    % N 6.19
Found:               66.4           6.1            6.2
IR Spectrum (CHCl₃)

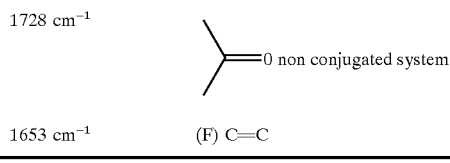

EXAMPLE 13

[16α, (±)-20,21-dinoreburnamenin-15-methanol and its acid maleate

STEP A: [16α, (±)]-spiro-[20,21-dinoreburnamenin-15(14H)-2' oxirane (isomer A) and its acid maleate 100 ml of tetrahydrofuran were added to a mixture of 19 g of trimethyl oxosulfonium iodide and 9.6 g of perfectly anhydrous potassium tert-butylate followed by stirring for 2 hours 30 minutes at 55° C. Then, 15 g of (16α)-20,21-dinoreburnamenin-15-(14H)-one (EP 0,013,315) in solution in 100 ml of tetrahydrofuran were added over 20 minutes, and the resultant mixture was stirred for one hour at ambient temperature. The insoluble part was filtered off and the filtrate was evaporated to dryness. The residue was washed with water, then chromatogrphed on silica (eluant: ethyl acetate) to obtain 10.54 g of isomer A melting at 182° C. and 2 g of isomer B melting at 167° C.

Salification: A solution of 575 mg of maleic acid in 50 ml of ethyl acetate was added to a solution of 1.39 g of the base (isomer A) in 100 ml of ethyl acetate. The resultant mixture was stirred for 4 hours, separated and washed with 100 ml of ethyl acetate to obtain 1.66 g of the desired product melting at 200° C.

STEP B: 16α, (±)]-20,21-dinoreburnamenin-15-methanol and its acid maleate a) Preparation of the Lithium Diisopropylamide 28.3 ml of butyllithium were ad(led dropwise to a solution of 6 ml of diisopropylamine in 100 ml of tetrahydrofuran stirred at –70° C. and the mixture was stirred for 20 minutes at 0°/+10° C.

b) The above solution was cooled to –70° C. and while maintaining this temperature, a solution of 9.9 g of isomer A of (16α)-20,21-dinoreburnamenin-15(14H)-2' oxirane in 150 ml of tetrahydrofuran was added, and the mixture was stirred for 30 minutes at –70° C., then for one hour at ambient temperature. 200 ml of iced water were added and the pH was adjusted to 7 by the addition of N hydrochloric acid. Extraction was done with methylene chloride and the extracts were washed with water, dried and evaporated to dryness under reduced pressure. The residue was taken up in a methylene chloride - methanol mixture (2-1) and the solution was filtered on florisil. The filtrate was evaporated to dryness to obtain 9.38 g of the expected product in the form of a base melting at 188° C.

Salification: A solution of 571 mg of maleic acid in 50 ml of boiling ethanol was added to a solution of 1.38 g of the base in 200 ml of an ethyl acetate - ethanol mixture (1-1). The mixture was stirred for 3 hours at ambient temperature and after separating, washing with ethanol and drying, 1.55 g of the desired product melting at 220° C. were obtained.

Analysis:        $C_{22}H_{24}N_2O_5$
Calculated:     % C 66.65    % H 6.10    % N 7.07
Found:              66.5            6.2            6.9
IR Spectrum (CHCl₃)
1608 cm⁻¹                    —OH
1653 cm⁻¹ (F)              —C=C— + C=N
1627 cm⁻¹                    + aromatic
Bohlmann bands

EXAMPLE 14

[16α, (±)]-N,N-dimethyl-20,21dinoreburnamenin-15-methanamine and its maleate

STEP A: [16α, (±)-14,15-dihydro-N,N-dimethyl-15-methanamine-20,21-dinoreburnamenin-15-ol At 0/–5° C., dimethylamine gas was bubbled through a solution of 4 g of the product of Step A of Example 13 in 80 ml of tetrahydrofuran until saturation was obtained and the resultant mixture was refluxed under pressure for 24 hours, then brought to dryness. The product was made into a paste in water, separated and dried under reduced pressure at 70° C. to obtain 4.37 g of the desired product melting at 200° C. which was used as is for the following step.

STEP B: [16α, (±)]-15-chloro-14,15-dihydro-N,N-dimethyl-20,21-dinoreburnamenin-15-methanamine 6.3 ml of a 1.5M solution of butyllithium were added slowly at –20° C. to a solution of 2.75 g of the product of Step A in 50 ml of tetrahydrofuran, and the mixture was stirred at 0° C. for 45 minutes. A solution of 0.74 ml of methane sulfonyl chloride in 10 ml of tetrahydrofuran were added followed by stirring for 15 hours at ambient temperature. After filtering, the filtrate was washed with tetrahydrofuran and concentrated to dryness. The residue was chromatographed on silica (eluant: methiylene chloride - methanol (95-5) to obtain 1.84 g of the expected product melting at 140° C.

STEP C: [16α, (±)]-N,N-dimethyl-20,21-dinoreburnamenin-15-methanamine and its maleate 4 ml of diazabicyclo-undecene (DBU) were added to a solution of 1.84 g of the product of Step B in 100 ml of toluene and the mixture was refluxed for 24 hours. The mixture was cooled, washed with water, dried and evaporated to dryness under reduced pressure. The residue was chromatographed on silica (eluant: ethyl acetate with 3% triethylamine) to obtain 1.07 g of the desired product in the form of a base melting at 111° C.

Salification: 337 mg of maleic acid in solution in 10 ml of boiling ethanol were added to a solution of 447 mg of the product in 430 ml of ethyl acetate. The mixture was stirred for 3 hours at ambient temperature, then for 10 minutes at 0° C. It was separated and washed with twice with 10 ml of ethanol. After drying under reduced pressure at 60° C., 570 mg of the desired product melting at 176° C. were obtained.

IR Spectrum:

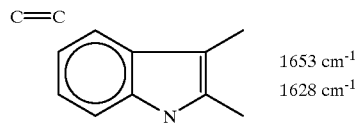

C=C    1653 cm⁻¹
       1628 cm⁻¹

Bohlmann bands
Analysis:     $C_{28}H_{33}N_3O_8$
Calculated:   % C 62.33    % H 6.16    % N 7.79
Found:            62.0          6.3          7.8

EXAMPLE 15

[16α, (±)-N-methly-20,21-dinoreburnamenin-15-methanamine and its maleate

Using the procedure of Example 14, 4 g of the product of Step A of Example 13 and monoethylamine were reacted to obtain the expected product.

EXAMPLE 16

[16α, (±)]-20,21-dinoreburnamenin-15-acetonitrile and its acid maleate 1.35 ml of diethylcyanomethyl phosphonate were added dropwise and an inert atmosphere to a suspension of 0.396 g of sodium hydride in 25 ml of tetrahydrofuran and the mixture was stirred for 30 minutes. 1 g of (16α)-20,21-dinoreburnamenine-15(14H)-one (EP 0,013,315) in solution in 20 ml of tetrahydrofuran were added, and the mixture was stirred for 3 hours at ambient temperature. The reaction mixture was poured over iced water and extracted with ethyl acetate. The extracts were washed with water, dried and chromatographed on silica (eluant: methylene chloride - acetonitrile 8-2) to obtain 740 mg of expected product in the form of a base. 200 mg of the base were dissolved hot in 30 ml of ethyl acetate and 5 ml of ethanol and then 80 mg of maleic acid were added. The mixture was stirred for 3 hours at ambient temperature, then dried at 70° C. under reduced pressure to obtain 220 mg of the expectd product melting at 250° C.

IR Spectrum (CHCl₃)

C=C aromatic        1656, 1633 cm⁻¹
C≡N                 2250 cm⁻¹
Bohlmann bands Analysis: $C_{19}H_{19}N_3$, $C_4H_4O_4$    molecular weight = 405.456
Calculated:    % C  68.13    % H  5.72    % N  10.36
Found:             68.3          5.7          10.4

EXAMPLE 17

Ethyl [16α, (±)](20,21-dinoreburnamenin-15-yl)-propynoate

STEP A: Ethyl (16α, (±) 14,15-dihydro-15-propiolate of 20,21-dinoreburnamenine-15-ol 6.4 ml of diisopropylamine were dissolved in 15 ml of tetrahydrofuran and 30 ml of a 1.6M solution of butyllithium in hexane were added at −10°/−20° C. under an inert atmosphere. The solution was stirred for 2 hours at −20° C., then for 15 minutes at 0° C. The solution was cooled to −50° C. and 4.8 ml of ethyl propiolate were added slowly. The mixture was stirred for 30 minutes at −50° C. and then 4 g of (16α) (±) 20,21-clinoreburnamenine-15(14H)-one (EP 0,013,315) in solution in 60 ml of tetrahydrofuran were added. The mixture was stirred at this temperature for one hour and the reaction mixture was poured into water and extracted with ethyl acetate. The organic phase was washed with water, dried and the solvents were eliminated under reduced pressure to obtain 6.1 g of product which was purified by chromatography on silica (eluant: methylene chloride - methanol 95-5) to obtain 3.7 g of the expected product melting at 228° C.

IR Spectrum (CHCl₃)
OH + associated     3595 cm⁻¹
C≡C                 2444 cm⁻¹

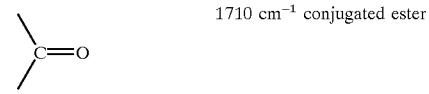
\C=O              1710 cm⁻¹ conjugated ester
/

C=C aromatic       1630, 1604, 1512 cm⁻¹

STEP B: Ethyl [16α, (±)](20,21-dinoreburnamenin-15-yl)-propynoate 3.7 g of the product of Step A were dissolved in 30 ml of tetrahydrofuran and 2.7 ml of triethylamin then 0.97 ml of mesyl chloride were added dropwise under an intert atmosphere. The mixture was stirred for 2 hours at ambient temperature and then the suspension was filtered. The filtrate was concentrated and 5.3 g of mesylate were collected. The product was dissolved in 130 ml of toluene and 1.49 ml of diazabicyclo-undecene were added. The mixture was stirred for 4 hours at ambient temperature and the reaction medium was concentrated under reduced pressure to obtain 6.5 g of product which was purified by chromatography on silica (eluant:hexane - ethyl acetate 8-2, then methylene chloride - methanol 95-5) to obtain the expected product melting at 100° C.

| Analysis: $C_{22}H_{22}N_2O_2$ | | | | | | |
|---|---|---|---|---|---|---|
| Calculated: | % C | 76.27 | % H | 6.4 | % N | 8.08 |
| Found: | | 76 | | 6.4 | | 7.8 |

EXAMPLE 18

(16α, (±) 20,21-dinoreburnamenin-15-acetamide and its acid maleate 10 ml of 5N sodium hydroxide, then 1 ml of hydrogen peroxide were added to 350 mg of (16α(±) 20,21-dinoreburnamenin-15-acetonitrile prepared as in Example 16 in solution in 10 ml of methanol and after stirring for 3 hours at ambient temperature, 50 ml of water were added to the suspension. The precipitate was separated off, washed with water and dried at 70° C. under reduced pressure to obtain 190 mg of the expected product in the form of a base melting at 160° C. 250 mg of the base obtained as above were dissolved in a mixture of 10 ml of ethyl acetate and 10 ml of ethanol and 87 mg of fumaric acid dissolved in 10 ml of boiling ethanol were added. The reaction medium was stirred for 2 hours at ambient temperature and, after drying under reduced pressure and crystallization from ethanol, 140 mg of the expected product melting at 230° C. were obtained.

| IR Spectrum (nujol): | | | | |
|---|---|---|---|---|
| C=O | | : 1672 cm$^{-1}$ | | |
| conjugated system | } | 1648, 1618, 1600 cm$^{-1}$ | | |
| aromatic NH$_2$ | | | | |
| Analysis: | $C_{19}H_{21}N_3O$, $C_4H_4O_4$ | | | |
| Calculated: | % C 65.24 | % H 5.95 | % N 9.92 | |
| Found: | 65.3 | 5.9 | 9.9 | |

EXAMPLE 19

(16α) (±) (14,15-dihydro-20,21-dinoreburnamenin-15-yliden) acetonitrile and its acid maleate Using the procedure of Example 16, 0.54 ml of diethyl-cyanomethyl phosphonate, 0.16 g of sodium hydride and 0.8 g of (16α) 20,21-dinoreburnamenin-15(14H)-one (EP 0,013, 315) were reacted to obtain 560 mg of the expected product in the form of a base and then 245 mg of acid maleate melting at 222° C. were prepared.

| IR Spectrum (CHCl$_3$) | | | | |
|---|---|---|---|---|
| C=C, C=N, aromatic | | 1656, 1631 cm$^{-1}$ | | |
| C≡N | | 2224 cm$^{-1}$ | | |
| Bohlmann bands | | | | |
| Analysis: $C_{19}H_{19}N_3$, $C_4H_4O_4$ | | | | |
| Calculated: | % C 68.13 | % H 5.72 | % N 10.36 | |
| Found: | 68.2 | 5.6 | 10.4 | |

EXAMPLE 20

(16α) (±) 20,21-dinoreburnamenin-15-acetic acid and its hydrochloride

Ethyl [16α(±)]-20,21-dinoreburnamenin-15-acetate prepared as in Example 12 in suspension in 55 ml of a 2N sodium hydroxide solution was heated for 13 hours at 100° C. and the mixture was cooled to 0° C. and acidified with concentrated hydrochloric acid. The crystals were separated off, washed with ethanol and dried at 50° C. to obtain 0.87 g of crude product which was crystallized from water to obtain the desired product melting at >260° C.

| IR Spectrum (nujol): | | | | |
|---|---|---|---|---|
| C=O: 1724 (max), 1700 cm$^{-1}$ (eq) | | | | |
| conjugated system | } | 1652, 1630, 1602, 1562 cm$^{-1}$ | | |
| + aromatic | | | | |
| Analysis: | $C_{19}H_{20}N_2O_2$, HCl | | | |
| Calculated: | % C 66.18 | % H 6.14 | % N 8.12 | % Cl 10.28 |
| Found: | 65.9 | 6.0 | 8.1 | 10.1 |

EXAMPLE 21

Hexyl (16α) (±) 20,21-dinoreburnamenin-15-acetate and its oxalate 0.8 g of the product of Example 20 in suspension in 75 ml of methylene chloride was stirred for 10 minutes, and 0.66 g of 1-ethyl-3-(3-dimethylaminopropyl)-carbodiimide hydrochloride were added. After stirring for 10 minutes, 0.28 g of hexanol were added, and the mixture was stirred for 16 hours at ambient temperature. The suspension was poured into water and the mixture was extracted with methylene chloride. The organic phase was washed with an aqueous solution of sodium bicarbonate, then with water, dried and the solvents were eliminated under reduced pressure. After chromatography on silica (eluant: methylene chloride - acetonitrile 9-1), 0.3 g of the expected product in the form of a base were obtained which was dissolved hot in 10 ml of ethyl acetate and 70 mg of oxalic acid dissolved hot in 5 ml of ethyl acetate were added. The suspension was stirred for one hour and the crystals were separated off, washed with ethyl acetate and dried to obtain 0.240 g of the expected salt melting at 190° C.

| Analysis: $C_{25}H_{32}N_2O_2$, $C_2H_2O_4$ | | | | | | |
|---|---|---|---|---|---|---|
| Calculated: | % C | 67.20 | % H | 7.10 | % N | 5.8 |
| Found: | | 67.4 | | 7.1 | | 5.5 |

EXAMPLE 22

(16α) (±) 1-(20,21-dinoreburnamenin-15-yl)-2-propanone

Using the procedure of Example 12, (16α),20,21-dinoreburnamenin-15(14H)-one (EP 0,013,315) and the appropriate phosphonate were reacted to obtain the expected product.

Using the procedure of Example 5 and starting with the derivative of the appropriate 20,21-dinoreburnamenine-15 (14H)-one and of the appropriate alkyl magnesium bromide, the following products were obtained:

EXAMPLE 23

(16α) (±) 9-methoxy-15-methyl-20,21-dinoreburnamenine.

EXAMPLE 24

(16α) (±) 15-(trifluoromethyl)-20,21-dinoreburnamenine.

The following products could also be obtained by a process of the invention defined above.

EXAMPLE 25

(16α) (±) 15-(fluoromethyl)-20,21-dinoreburnamenine.

EXAMPLE 26

Ethyl (16α) (±) 20,21-dinoreburnamenin-15-propanoate.

EXAMPLE 27

Ethyl (16α) (±) 20,21-dinoreburnamenin-15-carboxylate.

EXAMPLE 28

Ethyl (3α) 20,21-dinoreburnamenin-15-acetate.

EXAMPLE 29

Ethyl (16α) 20,21-dinoreburnamenin-15-acetate.

EXAMPLE 30

Dimethylethyl (16α) (±) 20,21-dinoreburnamenin-15-acetate.

EXAMPLE 31

Ethyl (16α) (±) alpha-methyl-20,21-dinoreburnamenin-15-acetate.

EXAMPLE 32
Pharmaceutical Composition

Tablets were prepared containing 25 mg of the product of Example 1 or 12 and sufficient excipient of lactose, talc, starch and magnesium stearate for a tablet of 300 mg.

PHARMACOLOGICL STUDY
1) Affinity for the Adrenergic Alpha 2 Receptors:

10 cortices removed from the brains of male rats weighing an average of 150 g were homogenized in 90 ml of 0.32 M sucrose. After centrifuging 1000 g of the homogenized mixture, for 10 minutes at 0° C.+4° C., the deposit was suspended in 240 ml of 50 mM Tris HCl pH 7.7 buffer, and centrifuged at 30,000 g for 15 minutes at 0°+4° C. The new deposit was suspended in 480 ml of 50 mM NaKPO$_4$ pH 7.4 buffer. Then, 2 ml of suspension were incubated for 45 minutes at 25° C. in the presence of $^3$H rauwolscine at a concentration of 0.15 nM:
I) alone or II) with increasing concentrations of the product under test or, III) to determine the non-specific fixation with non-radioactive phentolamine at a concentration of $10^{-5}$M.

The incubated suspensionis were filtered on Whatman GF/C and the filters were washed three times with 5 ml of NaKPO$_4$ pH 7.4 buffer at 0° C. The ratioactivity of the filters was measured by liquid scintillation. The affinity of the product tested for the adrenergic alpha2 receptors was determined relative to phentolamine as reference product.
CD=concentration of phentolamine inhibiting 50% of the specific fixation of $^3$H rauwolscine,
CX=concentration of the product under test inhibiting 50% of the specific fixation of $^3$H rauwolscine.

The relative affinity was calculated by the relation:

$$ARL = 100 \frac{CD}{CX}$$

| Product of Example | ARL |
|---|---|
| 2 | 367 |
| 5 | 456 |
| 7 | 980 |
| 11 | 343 |
| 12 | 942 |
| 13 | 346 |

These products showed a very strong affinity for the adrenergic alpha2 receptors.

2) Hypobaric anoxic

Male mice of CD$_1$ CHARLES RIVER type weighing 20 to 25 grams having gone without food for 6 hours were placed in a 2-liter chamber in which a pressure drop of 630 mm Hg was carried out according to the following kinetics:

| Time (s) | Pressure drop (mmHg) |
|---|---|
| 0 (TO) | 0 |
| 3.5 | 350 |
| 6 | 400 |
| 9 | 450 |
| 12 | 500 |
| 16 | 550 |
| 20 | 600 |
| 34 | 610 |
| 55 | 620 |

The survival time was measured from the time TO and over a maximum time of 3 minutes and it was about 70 seconds for the control animals. The rectal temperature was measured immediately before the determination of the survival time. The products were administered intraperitoneally at a dose of 10 mg/kg and in a volume of 10 ml/kg 60 minutes before the test and the control animals received the vehicle. The results were determined as a percentage of increase in the survival time relative to the control animals.

| Product of Example | % increase in survival time |
|---|---|
| 5 | 34 |
| 13 | 11 |
| 14 | 12 |

Various modifications of the products and method of the invention may be made without departing from the spirit or scope thereof and it should be understood that the invention is intended to be limited only as defined in the appended claims.

What we claim is:

1. A compound selected from the group consisting of all possible isomers or racemates of a compound of the formula

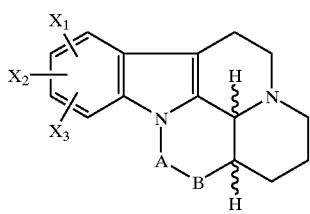

wherein $X_1$, $X_2$ and $X_3$ are individually selected from the group consisting of hydrogen, halogen, alkyl of 1 to 18 carbon atoms, alkenyl and alkynyl of 2 to 18 carbon atoms, alkoxy of 1 to 7 carbon atoms, —OH, —CF$_3$, —NO$_2$, —NH$_2$, mono and dialkylamino of 1 to 4 alkyl carbon atoms and phenyl; wherein

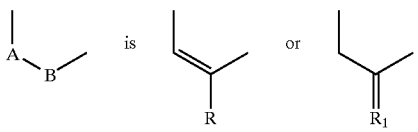

R is selected from the group consisting of alkyl of 1 to 7 carbon atoms optionally substituted with a member of the group consisting of hydroxy, amino, mono and dialkylamino, 1 to 3 halogens, —CN, carbamoyl and acyl of an organic carboxylic acid of 1 to 6 carbon atoms, alkynyl of 2 to 7 carbon atoms and phenyl, $R_1$ is

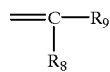

or =C=CH—$R_{10}$, $R_{10}$ is hydrogen or alkyl of 1 to 6 carbon atoms, one of $R_8$ and $R_9$ is selected from the group consisting of hydrogen, alkyl of 1 to 6 carbon atoms and cyano and the other is hydrogen or alkyl of 1 to 6 carbon atoms and its pharmaceutically acceptable salts with acid or bases.

2. A compound of claim 1 wherein $X_1$, $X_2$ and $X_3$ are hydrogen.

3. An antidepressant composition comprising an antidepressantly effective amount of at least one compound of claim 1 and an inert carrier.

4. The composition of claim 3 wherein in the active compound $X_1$, $X_2$ and $X_3$ are hydrogen.

5. A method for treating cerebral insufficiencies of anoxic or ischemic origin in warm blooded animals comprising administering to warm blooded animals a sufficient amount of at least one compound of claim 1 to treat cerebral insufficiencies of anoxic or ischemic origin.

6. The method of claim 5 wherein in the active compound $X_1$, $X_2$ and $X_3$ are hydrogen.

7. The method of treating cerebral insufficiencies of anoxic or ischemic origin in warm-blooded animals comprising administering to warm-blooded animals an amount of an active compound selected from the group consisting of [16α, (±)]-15-(1-propynyl)-20,21-dinoreburnamenine oxalate, [16α, (±)]-15-methyl-20-21,dinoreburnamenine, [16α, (±)]-14,15-dihydro-15-methylene-20,21-dinoreburnamenine acid maleate, [16α, (±)]-20,21-dinoreburnamenine-15-methanol acid maleate and [16α, (±)]-N,N-dimethyl-20-21-dinoreburnamenine-15-methanamine acid maleate to treat cerebral insufficiences of anoxic or ischemic origin.

8. A compound selected from the group consisting of [16α, (±)]-15-(1-propynyl)-20,21-dinoreburnamenine oxylate, [16α, (±)]-14,15-dihydro-15-methylene-20,21-dinoreburnamenine acid maleate, [16α, (±)]-2,21-dinoreburnamenine-15-methanol acid maleate and [16α, (±)]-N,N-dimethyl-20,21-dinoreburnamenine-15-methanamine acid maleate.

9. An anti-depressant composition comprising an anti-depressantively effective amount of a compound selected from the group consisting of [16α, (±)]-15-(1-propynyl)-20,21-dinoreburnamenine oxylate, [16α, (±)]-14,15-dihydro-15-methylene-20,21-dinoreburnamenine acid maleate, [16α, (±)]-2-,21-dinoreburnamenine-15-methanol acid maleate and [16α, (±)]-N,N-dimethyl-20,21-dinoreburnamenine-15-methanamineacid maleate and an inert pharmaceutical carrier.

10. A method of treating depression in warm-blooded animals comprising administering to warm-blooded animals an anti-depressively effective amount of a compound selected from the group consisting of [16α,(±)]-15-(1-propynyl)-20,21-dinoreburnamenine oxylate, [16α, (±)]-14,15-dihydro-15-methylene-20,21-dinoreburnamenine acid maleate, [16α, (±)]-2-,21-dinoreburnamenine-15-methanol acid maleate and [16α, (±)]-N,N-dimethyl-20,21-dinoreburnamenine-15-methenamine acid maleate.

\* \* \* \* \*